United States Patent [19]
Mynderse et al.

[11] Patent Number: 4,594,431
[45] Date of Patent: Jun. 10, 1986

[54] OCTAHYDROINDOLIZINEPROPANOIC ACIDS AND RELATED COMPOUNDS AS ENZYME INHIBITORS

[75] Inventors: Jon S. Mynderse, Indianapolis; David S. Fukuda, Brownsburg, both of Ind.

[73] Assignee: Eli Lilly Company, Indianapolis, Ind.

[21] Appl. No.: 519,360

[22] Filed: Aug. 1, 1983

[51] Int. Cl.$^4$ .................. C07D 209/00; C07D 221/00
[52] U.S. Cl. .................................... 546/138; 546/183
[58] Field of Search ............................... 546/138, 183

[56] References Cited

U.S. PATENT DOCUMENTS

| | | | |
|---|---|---|---|
| 3,274,202 | 9/1966 | Mohrbacher | 260/294 |
| 3,297,704 | 1/1967 | Mohrbacker | 260/294.3 |
| 3,494,929 | 2/1970 | Freed | 546/183 X |
| 4,046,889 | 9/1977 | Ondetti et al. | 424/244 |
| 4,154,935 | 5/1979 | Ondetti et al. | 546/189 |
| 4,316,905 | 2/1982 | Krapcho | 424/274 |
| 4,316,906 | 2/1982 | Ondetti et al. | 424/274 |
| 4,404,281 | 9/1983 | O'Connor et al. | 435/122 |
| 4,404,282 | 9/1983 | Nakatsukasa | 435/122 |
| 4,508,901 | 4/1985 | Mynderse et al. | 546/183 X |

OTHER PUBLICATIONS

Cushamn, D. W. et al.; Federation Proceedings, vol. 38, No. 13, Dec., 1979; pp. 2779–2782.
Derwent Abst. 25836 D/15 of EP 25–941 (ca 1981).
A. A. Patchett et al., Nature, 288: 280–283, (1980).
E. D. Thorsett et al., "Dipeptide Mimics. Conformationally Restricted Inhibitors of Angiotensin-Converting Enzyme", Biochemical and Biophysical Research Communications, vol. 111, No. 1, Feb. 28, 1983, pp. 166–171.

*Primary Examiner*—Joseph Paul Brust
*Attorney, Agent, or Firm*—William B. Scanlon; Arthur R. Whale

[57] ABSTRACT

Octahydro-5-oxoindolizine-6-propanoic acids and octahydro-6-oxopyrido[1,2-A]pyridine-7-propanoic acids, the decarboxy and related ester and perhydro derivatives thereof inhibit angiotensin I converting enzyme and are hypotensive agents. Hydrogenation of A58365 factors A and B, obtained by culturing *Streptomyces chromofuscus*, provides the ACE inhibitors. Also provided are O-acyl and O-sulfonyl derivatives of A and B factors which are useful in preparing deoxy factors A and B via hydrogenolysis.

4 Claims, No Drawings

OCTAHYDROINDOLIZINEPROPANOIC ACIDS AND RELATED COMPOUNDS AS ENZYME INHIBITORS

BACKGROUND OF THE INVENTION

This invention relates to compounds which inhibit angiotensin-converting enzyme. In particular, it relates to 3-carboxyoctahydro-5-oxo-6-indolizinepropanoic acids and related octahydropyrido[1,2-a]pyridine compounds.

The enzyme inhibitors of this invention are hypotensive agents and are useful for treating hypertension and pathological conditions arising from excessive angiotensin II levels and disease states wherein vasodilator therapy may be useful.

DESCRIPTION OF THE PRIOR ART

The decapeptide angiotensin I, previously referred to as hypertensin and angiotonin, is converted by the angiotensin-converting enzyme (ACE) to the octapeptide angiotensin II. The converting enzyme ACE splits off the C-terminal histadylleucyl residue of angiotensin I to form angiotensin II. Angiotensin II is a potent vasoconstrictor and acts directly on the adrenal gland to stimulate the release of aldosterones, M. Bodanszky, M. A. Ondetti, *Peptide Synthesis*, John Wiley, New York 1966, pp. 215–223; and Pumpus, "Angiotensin", *Renal Hypertension*, I. Page, J., McCubbin, eds. (Yearbook Medical Publishers, Chicago, IL, 1968), pp. 62–68. Angiotensin I is formed by the action of the enzyme renin on the substrate, angiotensinogen. The role of the renin-angiotensin system in the etiology of hypertension has been extensively studied; see, for example, *J. Med. Chem.*, 24, (4), 355–361 (1981), and the references cited therein.

SUMMARY

The ACE inhibitors known as A58365 factor A and A58365 factor B represented by the following structural formulae

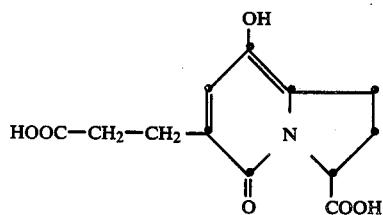

A

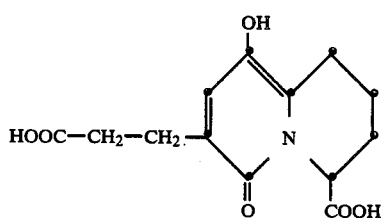

B produced by culturing *Streptomyces chromofuscus* NRRL 15098 are hydrogenated to the corresponding perhydro derivatives, 3-carboxyoctahydro-5-oxo-6-indolizinepropanoic acids and 4-carboxyoctahydro-6-oxo-7-pyrido[1,2-a]pyridinepropanoic acids, and the deoxy and decarboxy hydrogenolysis products, and the perhydro products of the latter. The hydrogenation and hydrogenolysis products obtained are useful hypotensive agents, in particular deoxy factor A obtained by hydrogenolysis of factor A. Certain acyl and sulfonyl derivatives of A58365 factors A and B are also provided as intermediates to deoxy factor A and deoxy factor B.

DETAILED DESCRIPTION

The 3-carboxyoctahydro(and tetrahydro)-5-oxo-6-indolizinepropanoic acids, the 4-carboxyoctahydro-6-oxo-7-pyrido[1,2-a]pyridinepropanoic acids, and hydroxy and ester derivatives thereof provided by this invention are represented by the following formula 1.

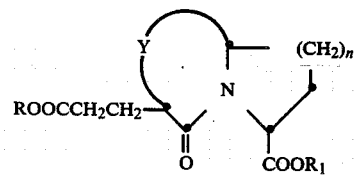

1.

wherein Y is

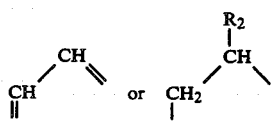

wherein
$R_2$ is hydrogen or hydroxy;
n is 1 or 2;
R and $R_1$ independently are hydrogen, $C_1$–$C_6$ alkyl, indanyl, phthalidyl, or an acyloxymethyl group represented by the formula

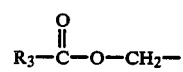

wherein $R_3$ is $C_1$–$C_4$ alkyl, phenyl, halophenyl, $C_1$–$C_4$ alkylphenyl, $C_1$–$C_4$ alkoxyphenyl, or 3,4-methylenedioxyphenyl; and when either or both of R and $R_1$ are hydrogen the pharmaceutically acceptable non-toxic salts thereof.

The 3-decarboxyoctahydro(and tetrahydro)-5-oxo-6-indolizinepropanoic acids and ester derivatives thereof are represented by the following structural formula 2

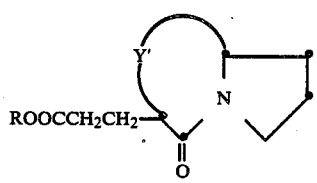

2 wherein
Y' is

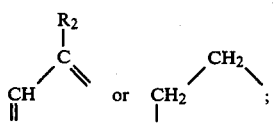

$R_2'$ is hydrogen or hydroxy;

R has the same meanings as defined for the formula 1; and when R is hydrogen the pharmaceutically acceptable non-toxic salts thereof.

In the above formulae the term "$C_1$–$C_6$ alkyl" refers to the straight and branched chain hydrocarbon radicals such as methyl, ethyl, n-propyl, iso-propyl, n-butyl, sec-butyl, t-butyl, n-amyl, iso-amyl, n-hexyl, 1,1-dimethylbutyl, and like radicals. The term "$C_1$–$C_4$ alkyl" refers to methyl, ethyl, n-propyl, isopropyl, n-butyl, sec-butyl, and t-butyl. The term "halophenyl" refers to the mono- or dihalophenyl groups such as 4-chlorophenyl, 3-chlorophenyl, 2-chlorophenyl, 3,4-dichlorophenyl, 3-bromophenyl, 4-bromophenyl, 2-fluorophenyl, 4-fluorophenyl, 3-iodophenyl, and the like; while the term "$C_1$–$C_4$ alkylphenyl" refers to the mono and dimethylphenyl groups such as 4-methylphenyl, 3-methylphenyl, 2-methylphenyl, 2,6-dimethylphenyl, 2,4-dimethylphenyl, 4-ethylphenyl, 3-iso-propylphenyl, 4-t-butylphenyl, 3-n-butylphenyl, 2-n-propylphenyl, and like groups; and "$C_1$–$C_4$ alkoxyphenyl" means 4-methoxyphenyl, 4-t-butyloxyphenyl, 3-ethoxyphenyl, 2-methoxyphenyl, 3,4-dimethoxyphenyl, 4-n-propoxyphenyl, and the like.

The compounds represented by the formula 1 wherein n is 1 are named 3-carboxytetrahydro (Y==CH—CH=) or octahydro $$(Y = -CH_2-\overset{R_2}{\underset{|}{CH}})\text{-5-oxo-6-indolizine-propanoic acids}$$

PS (R and $R_1$=H). Alternatively, and for convenience herein, these compounds are referred to as the hydrogenation products and deoxy products of A58365 factor A. The compounds of the invention obtained by the hydrogenation of factor A are the tetrahydrodeoxy factor A (3-carboxyoctahydro-5-oxo-6-indolizine-propanoic acid) represented by the formula 1a

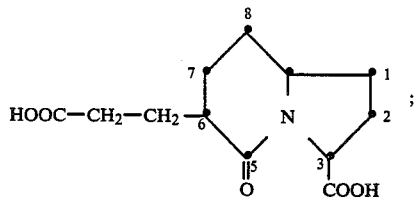

the tetrahydro factor A (3-carboxy-8-hydroxyoctahydro-5-oxo-6-indolizinepropanoic acid) represented by the formula 1b

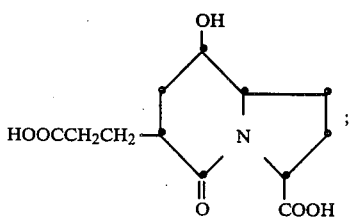

and the deoxy factor A (3-carboxy-tetrahydro-5-oxo-6-indolizinepropanoic acid) represented by the formula 1c

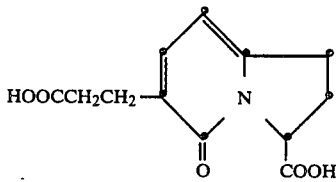

The compounds represented by the formula 1 wherein n is 2 are formally named as 4-carboxytetrahydro (Y==CH—CH=) or octahydro $$(Y = -CH_2-\overset{R_2}{\underset{|}{CH}})\text{-6-oxo-7-(pyrido[1,2-a]pyridine)propanoic acids.}$$

As with the indolizinepropanoic acids these compounds are conveniently referred to as hydrogenation products of A58365 factor B as follows. Tetrahydrodeoxy factor B (4-carboxyoctahydro-6-oxo-7-pyrido[1,2-a]pyridine-propanoic acid is represented by the formula 1d

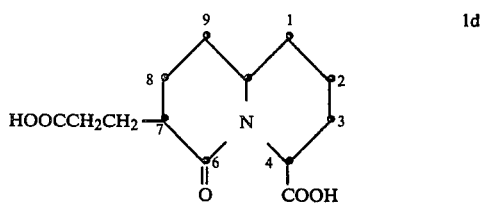

Tetrahydro factor B (4-carboxy-9-hydroxyoctahydro-6-oxo-7-pyrido[1,2-a]pyridinepropanoic acid) is represented by the formula 1e

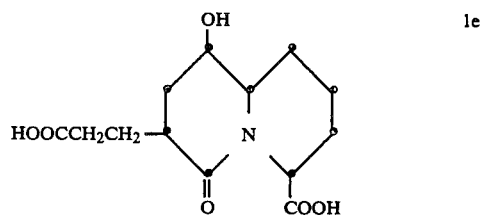

Deoxy factor B (4-carboxytetrahydro-6-oxo-7-pyrido[1,2-a]pyridinepropanoic acid) is represented by the formula 1f

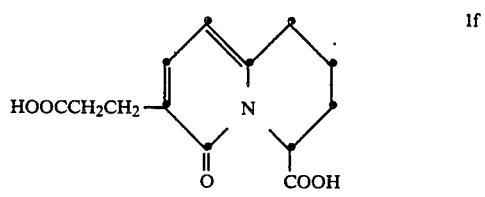

The compounds represented by the formula 2, the 3-decarboxyindolizinepropanoic acids, are obtained by the hydrogenation of factor A. They are decarboxy factor A, decarboxydeoxy factor A, and decarboxydeoxytetrahydro factor A represented respectively for the following formulae 2a, 2b, and 2c.

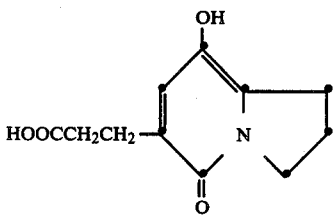

2a

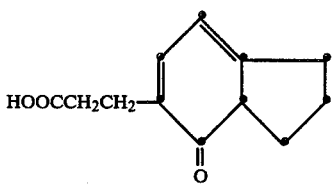

2b

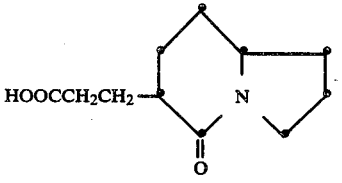

2c

The compounds of the invention, formula 1, are prepared by the hydrogenation of A58365 factors A (n=1) and B (n=2) represented by the following formula 3.

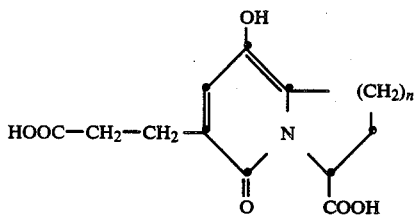

3

The decarboxy compounds represented by the formula 2 are obtained by the hydrogenation of factor A along with the compounds of formula 1 wherein n=1.

The hydrogenation of factor A when carried out in glacial acetic acid at a temperature between about 20° C. and about 75° C. under a hydrogen pressure up to about 100 psi in the presence of a platinum catalyst provides the compounds represented by the formula 1 wherein n=1, and the decarboxy compounds represented by the formula 2. The hydrogenation proceeds slowly and is generally carried out for about 24 hours.

The platinum catalyst used in the reduction can be in a variety of forms e.g. platinum oxide (prereduced), platinum supported on an inert support such as 5% or 10% platinum on carbon, alumina, silica or other inert support. Prereduced platinum oxide is a preferred catalyst. Preferably the catalyst is used in an amount about equal to the weight of factor A.

The hyrogenation is carried out in a suitable pressure vessel such as a heavy glass vessel or a stainless steel pressure bottle or autoclave. The reduction mixture is agitated during the reduction by stirring or by shaking or rocking the pressure vessel. The vessel and contents are desirably purged of air with hydrogen prior to reduction.

Under the above conditions some of the factor A remains unreduced and occurs in varying amounts in the reduction product mixture. The major hydrogenation product obtained with factor A under the above described hydrogenation conditions is tetrahydrodeoxy A (formula 1a). The tetrahydrodeoxy A product is obtained in three isomeric forms which can be separated from each other by HPLC, reversed phase $C_{18}$ silica chromatography. One of the isomers appears to have the following relative configuration as determined by analysis of its NMR spectrum.

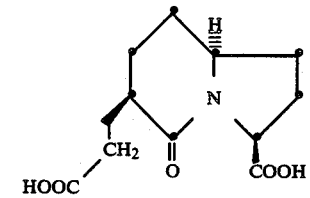

The second most abundant product obtained with factor A is deoxy A (formula 1c), while decarboxy factor A (formula 2a) is produced in lesser amounts. Decarboxydeoxy A (2b), tetrahydrodecarboxydeoxy A (2c), and tetrahydro A (1b) are produced in minor amounts.

The hydrogenation of A58365 factor B (formula 3, n=2) under the same conditions described above for the reduction of factor A provides as the major product tetrahydrodeoxy B (formula 1d) and lesser amounts of tetrahydro B (formula 1e). As with the reduction of factor A, some factor B is unreduced and occurs in the reduction product mixture. The major product, tetrahydrodeoxy factor B is produced in three isomeric forms which can be separated via $C_{18}$ reversed phase HPLC.

The hydrogenation of factor A when carried out in 1N hydrochloric acid at room temperature over platinum oxide in an atmosphere of hydrogen and, with the reduction being discontinued after one mole equivalent of hydrogen has been absorbed, provides deoxy factor A (1c) and tetrahydrodeoxy factor A (1a) along with unreduced factor A. No decarboxy product has thus far been observed under these conditions.

Tetrahydro factor A (1b) is obtained in higher yields when factor A is hydrogenated in methyl alcohol over a rhodium catalyst at a temperature between about 95° C. and 175° C. under about 500 psi of hydrogen pressure. The reduction is discontinued after about 12 hours at which time the reduction appears complete. The reduction also may be carried out in other solvents e.g. ethyl alcohol or n-propanol. The catalyst is preferably a supported rhodium catalyst such as 5% or 10% rhodium on carbon or other inert support e.g. alumina. When factor A as the free diacid (formula 3, n=1) is hydrogenated over rhodium in methyl alcohol a mixture of two isomers of the tetrahydro A diacid and two isomers of the tetrahydro A mono-methyl ester is obtained.

The dimethyl ester of factor A, when hydrogenated over rhodium under the same conditions used for the reduction of the diacid with rhodium, yields the dimethyl ester of tetrahydro factor A represented by the following formula.

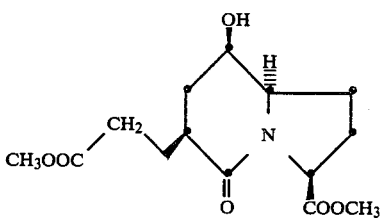

The relative configuration of the reduction product is the same as that of the tetrahydro factor A diacid obtained in the hydrogenation of A diacid over platinum in acetic acid.

The compounds of the invention (formulae 1 and 2) wherein R and $R_1$ are $C_1-C_6$ alkyl are prepared by the esterification of the diacid, formula 1, or the mono acid, formula 2. The esterification can be carried out by the Fischer esterification method by reacting the diacid factor A or B with a $C_1-C_6$ alcohol in the presence of an acid catalyst. Typical acid catalysts which can be used are boron trifluoride etherate, anhydrous hydrogen chloride, or p-toluene-sulfonic acid. The esterification is carried out in an inert solvent which may be the $C_1-C_6$ alcohol itself or may be another solvent such as diethyl ether. In an example of the esterification, the diacid is dissolved in methyl alcohol and about 1–3% anhydrous hydrogen chloride is bubbled into the solution. The acidic solution is then stirred for about 1–2 hours and the dimethyl ester is recovered.

Alternatively, the diacid (formula 1, $R=R_1=H$) can be esterified with the appropriate diazoalkane to obtain an ester of the invention.

The indan-5-yl esters of the invention are prepared by esterifying the desired acid with indane-5-ol for example by condensing the alcohol with the acid in the presence of a dehydrating agent such as a carbodiimide, for example dicyclohexylcarbodiimide.

The phthalidyl esters of the formulae 1 and 2 are prepared by reacting an alkali metal salt of the acid form (R and $R_1=H$) with bromophthalide. The reaction can be carried out in a suitable solvent such as dimethylformamide or dimethylacetamide by reacting equimolar amounts of the salt and bromophthalide.

The esters of the above formula wherein R or $R_1$ represents an acyloxymethyl group are prepared by reacting the desired acid as the sodium or potassium salt with an acyloxymethyl halide represented by the formula

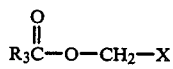

wherein X is preferably chloro or bromo and $R_3$ has the same meaning as defined hereinabove. Examples of acyloxymethyl chlorides and bromides which can be used are chloromethyl acetate, bromomethyl acetate, bromomethyl propionate, chloromethyl pivaloate, chloromethyl benzoate, bromomethyl 4-chlorobenzoate and like acyloxymethyl halides.

Following the preparation of diesters, any monoester present can be separated from the diester by solvent extraction at about pH 7. For example, the diester containing monoester is dissolved in a water immiscible organic solvent such as methylene chloride and the solution is washed with a dilute solution of a base. The neutral to basic wash removes the monoester in the form of its water soluble salt.

The individual monoesters represented by the above formula can be obtained by esterifying the desired acid with one equivalent of the alcohol. Any of the diester which is coproduced can be separated from the monoesters by solvent extraction at controlled pH as described above. The mixed monoesters obtained in the esterification are separated by conventional chromatographic methods for example, by preparative thin layer chromatography on silica gel or preferably, by HPLC.

The compounds of the invention form salts with pharmaceutically acceptable bases. Such bases include the alkali metal and alkaline earth metal hydroxides, carbonates, and bicarbonates e.g. sodium hydroxide, potassium hydroxide, calcium hydroxide, sodium carbonate, potassium carbonate and the like. Salts also may be prepared with ammonium hydroxide and suitable organic amines such as the monoalkylamines e.g. methylamine, ethylamine, isopropylamine; the primary cycloalkyl and aromatic amines e.g. cyclohexylamine and benzylamine; secondary amines such as diethylamine, dibenzylamine, and dicyclohexylamine; the hydroxylated alkylamines e.g. 2-hydroxyethylamine, di-(2-hydroxyethyl)amine, 3-hydroxypropylamine and di-(3-hydroxypropyl)amine; and other suitable amines such as procaine and abietylamine. Such salts are useful in the preparation of pharmaceutical formulations for use in treating hypertension.

The compounds of the invention represented by the formulae 1 and 2 wherein R and $R_1$ are hydrogen and the pharmaceutically acceptable non-toxic salts thereof inhibit angiotensin I converting enzyme (ACE) and thereby prevent the formation of the potent vasoconstrictor angiotensin II. The mono or di-biologically cleavable esters, such as the indanyl, phthalidyl and acetoxymethyl esters, are useful prodrug forms of the formulae 1 and 2 diacids. The $C_1-C_6$ dialkyl esters of the formula 1 and the $C_1-C_6$ alkyl mono esters of the formula 2 are useful forms of the corresponding mono or diacids which can be used in the separation and purification of reduction products and the isomers thereof. The mono $C_1-C_6$ alkyl esters of the formula 2 and the salts and biologically cleavage esters thereof are less active than the mono or diacid compounds in inhibiting ACE.

The ACE inhibition activity of the compounds of the invention can be demonstrated in in vitro tests carried out with isolated guinea pig ileum. The in vitro tests are carried out as follows: segments (2–3 cm long) of the guinea pig ileum are mounted longitudinally in 10 ml. isolated tissue baths containing Krebs' solution having the following composition (mmol. concentrations): sodium chloride, 118.2; potassium chloride, 4.6; calcium chloride dihydrate, 2.5; monopotassium phosphate, 1.2; magnesium sulfate, 1,2; dextrose, 10.0; and sodium bicarbonate, 24.8. In all experiments tissues are maintained at 37° C. and aerated with 95% oxygen and 5% carbon dioxide. The ilea are mounted between two electrodes consisting of a stainless steel rod (bottom) and a circular platinum wire (top). Square wave impulses (0.1 Hz) of supramaximal voltage (40 v) and 0.7 msec duration are provided by a Grass S44 stimulator. Tissues are equilibrated for approximately one hour at 1 g of applied force. Isometric responses can be recorded on Beckman Dynographs.

Concentration-response curves to 3 or 4 concentrations of angiotensin I are generated. Tissues are then equilibrated with the test solution ($10^{-6}$ to $10^{-5}$M) and concentration-response curves to angiotensin I are reassessed.

The ACE inhibitory activity also can be demonstrated by the lowering of the blood pressure in sodium depleted rats treated with test compounds.

The ACE inhibitory compounds of the invention as described hereinabove are useful for lowering the blood pressure in hypertensive mammals. The compounds or the pharmaceutically acceptable non-toxic salts thereof are administered to a hypertensive host in a blood pressure lowering dose of between about 200 mg. and about 2,000 mg. For parenteral administration the compound or its salt or biologically cleavable ester is dissolved or suspended in a physiologically acceptable fluid for injection, either intramuscularly or intravenously. Suitable fluids or diluents such as Water-For-Injection, 0.9% saline, 5% glucose or other fluid may be used. For oral administration the compound or a salt or ester thereof may be formulated in gelatin capsules, tablets or liquid suspensions. The administration can be carried out with a single daily dose or multiple daily doses.

Preferred ACE inhibitors are represented by the formula 1 wherein R and $R_1$ are hydrogen, n is 1 or 2 and Y is =CH—CH=.

This invention also provides derivatives of the A58365 factors A and B which are useful intermediates for the preparation of deoxy factor A and deoxy factor B (formulae 1c and 1f, respectively). The derivatives are represented by the following formula 4

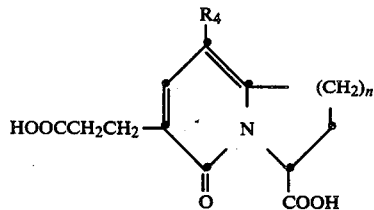

wherein
n is 1 or 2;
$R_4$ is $C_2$-$C_5$ alkanoyloxy, halo substituted $C_2$-$C_5$ alkanoyloxy, or a sulfonyloxy group

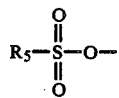

wherein $R_5$ is $C_1$-$C_4$ alkyl or a phenyl group

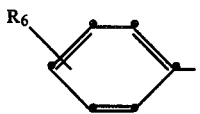

wherein $R_6$ is hydrogen, $C_1$-$C_4$ alkyl, $C_1$-$C_4$ alkoxy, nitro, or halogen.

In the above formula 4, "halogen" refers to fluoro, chloro, bromo or iodo; "$C_2$-$C_5$ alkanoyloxy" refers to acetoxy, propionyloxy, butyryloxy, isobutyryloxy, and the like; "halo substituted $C_2$-$C_5$ alkanoyloxy" refers to trichloroacetoxy, chloroacetoxy, bromoacetoxy, 3-chloropropionyloxy, 3-bromobutyryloxy, and like groups; "sulfonyloxy" refers to methanesulfonyloxy, ethanesulfonyloxy, n-butanesulfonyloxy, and like lower alkylsulfonyloxy groups; and to phenylsulfonyloxy and the lower alkyl, lower alkoxy, nitro, and halo substituted phenylsulfonyloxy groups such as p-toluenesulfonyloxy, p-chlorophenylsulfonyloxy, m-bromophenylsulfonyloxy, p-methoxyphenylsulfonyloxy, p-nitrophenylsulfonyloxy, and like substituted groups.

The compounds represented by the formula 4 are prepared in general by the acylation or sulfonylation of factor A and factor B. For example, the alkanoyloxy derivatives are prepared by acylating the hydroxy group of factor A or factor B with an anhydride of the desired $C_1$-$C_5$ alkyl carboxylic acid in the presence of a tertiary amine such as triethylamine or, preferably, pyridine. For example, factor A is reacted with acetic anhydride in the presence of pyridine to form the O-acetyl factor A. Alternatively, the acylation may be effected by reacting the desired carboxylic acid halide with the factor in the presence of an acid binding agent, e.g. pyridine.

Sulfonylation of the factors A and B is carried out by reacting an alkylsulfonyl halide, phenylsulfonyl halide, or substituted phenylsulfonyl halide with the desired factor in the presence of an acid scavenger, e.g. a tertiary amine such as triethylamine or pyridine. For example, factor A is reacted with methanesulfonyl chloride in the presence of triethylamine to provide the mesylate of factor A. The tosylate of factor A may be prepared in the same manner with tosyl chloride.

The acylation and sulfonylation can be carried out in a suitable polar organic solvent or aqueous-organic solvent mixtures. Suitable solvents include acetonitrile, tetrahydrofuran, acetone, methylethyl ketone, dimethylacetamide, dimethylformamide, and like common solvents which are unreactive toward the acylating or sulfonylating agent.

The O-acyl and O-sulfonyl derivatives of factors A and B (formula 4) undergo hydrogenolysis with hydrogen over platinum catalyst to afford the deoxy A and deoxy B (formulae 1c and 1f, respectively). The hydrogenolysis is carried out preferably over prereduced $PtO_2$ in about 1N hydrochloric acid at a temperature between about 20° C. and about 45° C., preferably at room temperature. Low hydrogen pressures of about 1-2 atmospheres are sufficient. Generally, the catalyst is used in an amount equal in weight to the weight of the acylated or sulfonylated factor A or B used in the reduction.

The hydrogenolysis of the factor A or B derivative (formula 4) is a preferred method for preparing the deoxy factor A and deoxy factor B. During the hydrogenolysis of an acyl derivative of factor A, a lesser amount of the tetrahydrodeoxy factor A is obtained along with a minor amount of factor A. The factor A appears to arise in the reduction mixture by virtue of hydrolysis of the derivative. The factor A and the deoxy A and tetrahydrodeoxy A are separated via reversed phase $C_{18}$ silica HPLC.

The compounds of the formula 4 are useful intermediates for preparing the ACE inhibitors deoxy factor A and deoxy factor B represented by the formulae 1c and 1f. In addition to their use as intermediates, the compounds represented by the formula 4 wherein $R_4$ is a $C_2$-$C_5$ alkanoyloxy group and the pharmaceutically acceptable salts thereof are also active ACE inhibitors. In particular, a preferred acyl derivative is the O-acetyl factor A which has demonstrated ACE inhibition activity in the same tests in which factor A and the reduction products of factors A and B of formula 1 demonstrated activity. Accordingly, the O-acyl derivatives of the formula 4 and the pharmaceutically acceptable, non-toxic salts and biologically active esters thereof are useful hypotensive agents in the treatment of hypertension.

The A58365 factors A and B (formula 3) which are used as starting materials for preparing the ACE inhibitors of this invention are obtained by culturing a new strain of *Streptomyces chromofuscus* NRRL 15098 as described in co-pending applications serial Nos. 409,765 now U.S. Pat. No. 4,404,281 and 409,764 now U.S. Pat. No. 4,404,282, filed Aug. 19, 1982. The compound of the formula 3 wherein n is 1 is designated in the co-pending application as A58365 factor A, while the compound of the formula 3 wherein n is 2 is designated as A58365 factor B. As described in the co-pending applications, the compounds of the formula 3 are prepared by culturing *Streptomyces chromofuscus* NRRL 15098 under aerobic fermentation conditions in an aqueous nutrient culture medium containing assimilable sources of carbon, inorganic salts and nitrogen. The culture medium employed in the fermentation can be any one of a number of media since the microorganism is capable of utilizing energy from a variety of nutrient sources. For example, a variety of carbohydrates including sugars and starches can be included in the culture medium to supply the carbon requirements of the microorganism. Likewise, various sources of nitrogen such as the amino acids, distillers extracts, meat peptones, and casein hydrolysates can be employed in the culture medium. In the interest of economy in production, optimal yield, and ease of isolation of the ACE factors, certain culture media are preferred. For example, one of the preferred sources of carbon is potato dextrin, although various sugars such as glucose or fructose may also be used. Preferred sources of nitrogen are peptones and the hydrolysates of casein. As is common in the fermentation of microorganisms, nutrient inorganic salts can be incorporated in the culture medium for the production of the ACE factors. Such inorganic salts are the customary salts capable of yielding sodium, potassium, ammonium, calcium, phosphate, chloride, carbonate, and like ions. Trace elements may also be added to the fermentation medium; however, these are commonly added in sufficient trace amounts as constituents of other ingredients added to the media.

During the fermentation of *S. chromofuscus* NRRL 15098 to produce the A58365 factors, cobaltous ion or other divalent cation is added to the fermentation medium. Cobaltous chloride is a convenient source of divalent cobalt. The divalent cation such as cobaltous ion is added in minor amounts, for example, the addition of between about 5 mg. and about 15 mg. of cobaltous chloride hexahydrate per liter of medium is sufficient.

It has been found that the production of the A58365 factor A by *S. chromofuscus* is greatly enhanced by the addition of proline to the fermentation medium. Generally, between about 1 g. and about 6 g. of proline per liter of fermentation broth is sufficient. It has also been found that when, in addition to proline, the culture medium is supplemented with lysine, preferably L-lysine, A58365 factor B is produced in enhanced yields and becomes the more abundant factor produced. Preferably in the production of factor B the culture medium is supplemented with between about 1 g. and about 6 g. of proline per liter and between about 1 g. and about 3 g. of lysine per liter of culture medium.

The fermentation can be carried out at temperatures between about 23° C. and about 30° C. However, best yields are obtained when the fermentation is carried out at 25° C. During the fermentation the pH of the medium increases. Generally, the initial pH of the broth is adjusted to about 7, and the terminal pH is about 8 to 8.3.

The fermentation is carried out under aerobic conditions. Sterile air is passed through the fermentation medium with stirring during the course of the fermentation. For best results, the dissolved oxygen level in the fermentation medium should be maintained at approximately 30 to 40% of air saturation.

An antifoam agent is generally beneficial to prevent excess foaming and any of the commonly employed antifoam agents such as the silicone antifoam agents can be employed in the fermentation.

The production of the ACE inhibitory factors during the course of the fermentation is followed by high performance liquid chromatography assay of an aliquot of the broth withdrawn from time to time. Peak production generally occurs between about 70 and about 90 hours into the fermentation. The assay is carried out employing as the stationary phase a 4 mm.×300 mm. $\mu$ Bondapak C18 column (Waters Associates), and a mobile phase comprising acetonitrile:formic acid:water (6:0.3:93.7, v:v:v). The flow rate is 2.5 ml./min. Detection of the factors is carried out with a Schoeffel model FS970 spectrofluorometer by employing the wave length $\lambda exc=327$ nm, and a 370 nm. emmission cut off filter.

In carrying out the fermentation, a small volume of vegetative medium is inoculated with a lyophilized pellet of *S. chromofuscus* NRRL 15098. Incubation of the culture is carried out at about 30° C. and, following the attainment of good growth which generally occurs in about two days, the vegetative medium or portions thereof are employed to inoculate a large scale medium known as a "bump" medium. The "bump" medium is an intermediate-size medium used as a large inoculum for large scale fermentation tanks. In general, the "bump" medium has the same or approximately the same composition as the vegetative medium. The initial small-volume vegetative medium can be a highly nutritive medium used for culturing microorganisms. A suitable vegetative medium which provides good growth of *S. chromofuscus* NRRL 15098 is composed of trypticase soy broth plus approximately 1% glucose. Trypticase soy broth is a commercially available soybean-casein digest containing pancreatic digest of casein, soy peptone (a digest of soybeans), sodium chloride, dipotassium phosphate and glucose.

Alternatively, the lyophilized pellet of *S. chromofuscus* can be initially grown on an agar slant and, following growth, spores on the agar slant are transferred under sterile conditions to a vegetative medium. The grown vegetative medium can then be employed as described above for the inoculation of intermediate size "bump" media.

The microorganism employed in the method for producing the ACE inhibitors of this invention has been identified as a new strain of *Streptomyces chromofuscus* (Preobrashenskaya, Blinov and Ryabova 1957), Pridham, Hessetine and Benedict, "A Guide for the Classification of Streptomycetes According to Selected Groups", *Appl. Microbiol.* 6:52–59, (1957).

The new strain of *S. chromofuscus* has been deposited without restriction as to public availability in the permanent collection of the Agricultural Research Culture Collection, Northern Regional Research Center, Department of Agriculture, 1815 North University Street, Peoria, IL 61604, where it has been assigned the accession number NRRL 15098.

The A58365 factors A and B are isolated from the fermentation medium and are separated from one another by chromatography. The isolation and separation of the factors is carried out as follows. The whole fermentation broth is acidified to about pH 2.0 and is filtered to remove the mycelium and other insolubles. A filter aid is desirably used and enhances the rate of filtration. Following the filtration the pH of the filtered broth is adjusted to about pH 7.0 with a base such as sodium hydroxide. In a preliminary chromatography to remove inactive neutral impurities, the neutral filtered broth is treated with a nonfunctional polymeric reticular resin, for example, a polystyrene resin such as Diaion HP-20 (Mitsubishi Chemical Co.) or a XAD resin (Rohm and Haas, Philadelphia, PA). The neutral broth may be passed through a column packed with the resin or, alternatively, the resin may be added to the neutral broth in a suitable vessel and stirred with the broth to adsorb the inactive impurities. In this preliminary purification of the broth the resin is used in an amount corresponding to about one-tenth of the volume of the broth. Preferably, the resin is stirred in the neutral broth for about two hours and is then separated by filtration. The pH of the resin-treated broth is then lowered to about pH 2.0–3.0 with an acid such as hydrochloric acid and the acidified broth is chilled and filtered to remove an inactive precipitate.

The acidic, polished broth is next chromatographed over a nonfunctional resin, preferably Diaion HP-20. The acidic broth is poured onto a column packed with the HP-20 resin and the effluent discarded. After the column is washed with a dilute acid, preferably 0.3% aqueous formic acid, the A58365 factors are eluted by gradient elution employing a gradient from water:formic acid (99.7:0.3, % by vol.) to acetonitrile:water:formic acid (20:79.7:0.3, % by vol.). Multiple fractions are collected with factor A eluting in the early active fractions and factors B and C eluting in the later active fractions. The course of the chromatography is followed by the HPLC assay described herein.

The A58365 factor A containing factors are pooled and concentrated by evaporation. The concentrate is then applied to an acidic resin such as a polystyrene sulfonic acid resin in the acid cycle, for example, Dowex 50W resin (Dow Chemical Co.). Factor A is washed from the resin with deionized water in multiple fractions. The factor A containing fractions are combined and concentrated by evaporation.

The acidic (pH 2-3) concentrate of factor A is filtered and then subjected to reverse phase preparative HPLC on $C_{18}$ silica gel such as octadecylsilanized Whatman LP-1 or Water's Assoc. $C_{18}$ silica gel. The column is developed first with aqueous formic acid (0.3:99.7% by vol.), next with acetonitrile:formic acid:water (1.0:0.3:98.7% by vol.), and finally with acetonitrile:formic acid:water (2.5:0.3;97.2% by vol.). The fractions containing factor A are pooled and concentrated by evaporation.

The factor A concentrate from the HPLC column is then chromatographed over an anion exchange resin such as 100–200 mesh BioRex 5 resin in the chloride cycle (BioRad Laboratories, Richmond, CA). The column is eluted with about 0.2M to about 0.5M sodium chloride and pure factor A containing fractions are combined. The pooled fractions are acidified to about pH 2.2–2.5 with acid, eg. 1N hydrochloric acid, and are passed over Diaion HP-20 resin to remove salts present in the fractions from the anion exchange chromatography. Prior to use, the HP-20 resin is prepared with 0.01N hydrochloric acid. Factor A is eluted by first washing the column with dilute acid (pH 2.3), next with water and finally with aqueous acetonitrile (15:85% by volume). The factor A containing fractions are pooled, concentrated by evaporation, and the concentrate is lyophilized to provide pure factor A as an amorphous white powder.

The combined fractions containing factors B and C, obtained as described above by gradient elution from the HP-20 chromatography of polished broth, are concentrated to a smaller volume by evaporation. The concentrate of factors B or C is next chromatographed over a polystyrene polysulfonic acid resin such as Dowex 50W (H+) (Dow Chemical Co.). Factors B or C are washed from the resin with deionized water. The fractions containing factor B are combined and concentrated. Factor C containing fractions are likewise combined and concentrated.

The concentrates of factors B and C are separately purified by reversed phase HPLC using $C_{18}$ silica gel eg., octadecylsilanized Whatman LP-1 silica gel. Factor B is eluted from its chromatogram using first formic acid:water (0.3:99.7% by vol.), next acetonitrile:formic acid:water (6.0:0.3:93.7%), and finally acetonitrile:formic acid:water (15.0:0.3:84.7% by vol.). Factor C may be eluted from its chromatogram using similar solvent systems containing, however, a higher concentration of acetonitrile in the solvent mixture. The active fractions off the chromatograms are combined and concentrated.

The concentrates of factors B and C can be further purified by following the procedures described above for factor A. For example each concentrate is chromatographed over an anion exchange resin, the respective eluents acidified, desalted over a non-functional resin, and the desalted eluents lyophilized.

Factor A is produced in greater abundance than factors B and C. Factor B in turn is produced in greater amounts than is Factor C.

The following Examples further define and illustrate the present invention.

EXAMPLE 1

Catalytic Hydrogenation of A58365A

To a solution of 600 mg. of A58365 factor A in 40 ml. of glacial acetic acid were added 600 mg. of platinum oxide catalyst and the suspension was hydrogenated at room temperature for 24 hours under 60 psi hydrogen pressure. The catalyst was separated from the reduction mixture by filtration and the filtrate was lyophilized to yield 583 mg. of the reduction product mixture.

The reduction product mixture was separated into the individual reduction products by reversed phase HPLC as follows. A 1"OD×12" Zorbax ODS (Dupont) column ($C_{18}$ bonded phase, particle size 12µ) was used. The gradient employed was as follows:

|    | Solvent | % by Volume | Volume (ml) |
| --- | --- | --- | --- |
| A: | acetic acid-water | 0.2:99.8 | 120 |
| B: | acetonitrile-acetic acid-water | 8:0.2:91.8 | 2,040 |
| C: | acetonitrile-water | 50:50 | 220 |

The reduction product mixture (583 mg.) was dissolved in 3 ml. of mobile phase A and injected onto the column. The flow rate during the chromatography was 10 ml./min. and multiple 20 ml. fractions were collected. The fractions were monitored via analytical HPLC using a wavelength of 210 nm and 254 nm. Fractions containing the same product were pooled, concentrated and lyophilized as follows.

| Fractions' Pooled | Product | Weight (mg.) |
|---|---|---|
| 17–22 | Factor A unreduced | 133.6 |
| 27–31 | Decarboxy A | 10.8 |
| 36–41 | Deoxy A | 40 |
| 58–86 | Tetrahydrodeoxy A (predominant isomer) | 182 |
| 87–96 | Decarboxydeoxy A | 5.5 |

The remaining fractions collected were pooled, concentrated by evaporation and rechromatographed using the same column. The mobile phase was approximately 140 ml. of 0.2% aqueous formic acid followed by 10% acetonitrile in 0.2% aqueous formic acid. The flow rate was 10 ml./min. and 20 ml. fractions were collected. Fractions were pooled, concentrated and lyophilized to provide the reduction products tetrahydro factor A and tetrahydrodeoxydecarboxy factor A as follows.

| Fraction (s) | Product | Weight (mg.) |
|---|---|---|
| 17 | Tetrahydro A | 7.3 |
| 34–36 | Tetrahydrodeoxy A minor isomer 1 | 4.6 |
| 37 | Tetrahydrodeoxy A minor isomer 2 | 1.3 |
| 40–44 | Tetrahydrodeoxy A predominant isomer | 8.5 |
| 65–67 | Tetrahydrodeoxydecarboxy A | 17.4 |

The following analytical and spectral data were obtained with the isolated products.

Deoxy factor A (formula 1c)
$^1$H NMR (270 MHz, D$_2$O): δ (ppm) 2.38 (m, 1H), 2.64 (m, 1H), 2.68 (t, 2H), 2.80 (t, 2H), 3.21 (t, 2H), 5.15 (dd, 1H), 6.48 (d, 1H), and 7.55 (d, 1H).

$^{13}$C NMR (67.9 MHz, D$_2$O): δ (ppm) 25.9, 1C; 26.9, 1C; 30.8, 1C; 33.6, 1C; 63.8, 1C; 104.6, 1C; 127.7, 1C; 141.8, 1C; 151.1, 1C; 163.3, 1C; 175,3, 1C; and 178.4, 1C.
FD/MS: (M+H)$^+$=252.

High Resolution Fast Atom Bombardment Mass measurement: 252.08887—C$_{12}$H$_{14}$NO$_5$.

UV Spectrum (methyl alcohol): $\lambda_{max}$=234 nm (ε=5600), 306 nm (ε=7500). No shift of $\lambda_{max}$ occurred on the addition of base.

Optical Rotation: [α]$_{589}$$^{25°}$=−216.3° (c=5 mg/ml, H$_2$O). [α]$_{365}$$^{25°}$=−1391.1 (c=5 mg/ml, H$_2$O).

Decarboxy Factor A (formula 2a)
$^1$H NMR (360 MHz, D$_2$O): δ (ppm) 2.28 (2H, q, 7.3, 7.3, 7.3, 7.3 Hz), 2.67 (2H, t, 7.3, 7.3 Hz), 2.78 (2H, t, 7.3, 7.3 Hz), 3.13 (2H, t, 7.3, 7.3 Hz), 4.18 (2H, t, 7.3, 7.3 Hz), and 7.32 (1H, s).
FD/MS: (M+)=223.
UV Spectrum (methyl alcohol):

| neutral and acidic pH $\lambda_{max}$ | = 230 nm (ε = 4,000) |
| | = 317 nm (ε = 5,900) |
| basic pH | = 245 nm (ε = 6,000) |
| | = 355 nm (ε = 6,200) |

Decarboxydeoxy Factor A (formula 2b)
$^1$H NMR (360 MHz, D$_2$O): δ (ppm) 2.23 (2H, p, 7.3, 7.3, 7.3, 7.3 Hz), 2.64 (2H, t, 7.3, 7.3 Hz), 2.79 (2H, t, 7.3, 7.3 Hz), 3.15 (2H, t, 7.3, 7.3 Hz) 4.15 (2H, t, 7.3, 7.3 Hz), 6.46 (1H, d, 7.3 Hz), and 7.49 (1H, d, 7.3 Hz).
FD/MS: (M+)=207.

Tetrahydrodeoxy Factor A (formula 1a)
Predominant Isomer
$^1$H NMR (270 MHz, D$_2$O): δ (ppm) 1.49–1.74 (2H, m), 1.74–1.88 (2H, m), 1.88–2.31 (6H, m), 2.44 (1H, m), 2.52 (2H, t), 3.65 (1H, m), 4.38 (1H, d).
Minor Isomer 1
$^1$H NMR (270 MHz, D$_2$O): δ (ppm) 1.39–1.62 (2H, m), 1.70–1.88 (3H, m), 1.89–2.12 (3H, m), 2.18 (1H, q), 2.44 (2H, m), 2.52 (2H, t), 3.67 (1H, m), 4.37 (1H, t).
Minor Isomer 2
$^1$H NMR (270 MHz, D$_2$O): δ (ppm) 1.33–1.50 (1H, q), 1.50–1.70 (2H, m), 1.70–1.96 (2H, m), 1.97–2.29 (4H, m), 2.48 (4H, m), 3.71 (1H, m), 4.40 (1H, dt).
The FD/MS for all three isomers was (M+H)$^+$=256.

Another preparation of the predominant isomer of tetrahydrodeoxy factor A was obtained from another reduction of factor A. The following data were obtained with this preparation.

Optical rotation [α]$_D$$^{25}$−32.2° (C=10 mg/ml, CH$_3$OH).

Field Desorption Mass Spectral Analysis: 256 (M+H)$^+$.

$^{13}$C NMR (D$_2$O, 67.9 MHz): δ 25.63 (1C, t), 26.09 (1C, t), 27.84 (1C, t), 28.71 (1C, t), 31.95 (1C, t), 32.69 (1C, t), 39.24 (1C, d), 59.44 (1C, d), 60.80 (1C, d), 175.49 (1C, s), 176.65 (1C, s), and 178.93 (1C, s).

$^1$H NMR (D$_2$O, 360 MHz): δ1.56 (1H, m), 1.64 (1H, m), 1.78 (1H, m), 1.80 (1H, m), 1.96 (1H, m), 2.04 (1H, m), 2.05 (1H, m), 2.06 (1H, m), 2.13 (1H, m), 2.21 (1H, m), 2.40 (1H, m), 2.49 (2H, m), 3.62 (1H, m), and 4.34 (1H, dd).

Tetrahydro Factor A (formula 1b)
Field Desorption Mass Spectrum: (M+H)$^+$=272.
$^1$H NMR (270 MHz, D$_2$O): δ(ppm) 1.67 (1H, m), 1.78 (1H, m), 2.12 (4H, m), 2.29 (1H, m), 3.52 (4H, m), 3.94 (1H, t), 4.23 (1H, m), 4.42 (1H, d).

Tetrahydrodecarboxydeoxy Factor A (formula 2c)
FD/MS: (M+H)$^+$=212.
$^1$H NMR (270 MHz, D$_2$O): δ(ppm) 1.20–2.20 (10H, highly overlapped), 2.46 (3H, m), 3.45 (3H, m).

EXAMPLE 2

Hydrogenation of A58365 factor B

To a solution of 157 mg. of A58365 factor B (ca 60% purity) in 40 ml. of glacial acetic acid were added 160 mg. of platinum oxide catalyst. The mixture was placed in a Parr hydrogenation apparatus and the vessel pressurized with hydrogen to 60 psi. The hydrogenation was carried out at 60° C. for 17 hours. The mixture was cooled to room temperature, the catalyst separated by filtration, and the filtrate was lyophilized to provide 185.9 mg. of impure reduction product mixture. The mixture was purified and the reduction products separated from each other by reversed phase C$_{18}$ chromatography carried out as follows.

The column used was a 1"OD×12" Zorbax ODS column (particle size 12μ). The mobile phase was the solvent mixtures: A: 0.2% formic acid-water; B: 0.2% formic acid-10% acetonitrile-water; C: 0.2% formic acid-12.5% acetonitrile-water; D: 50% aqueous acetonitrile.

The flow rate was 10 ml./min. and 140 fractions of 20 ml. volume were collected. Fractions 1–14 were collected with solvent A; 15–44 with solvent B; 45–117 with solvent C; and the remainder with aqueous 50% acetonitrile. The fractions were analyzed with analytical HPLC using 210 nm. wavelength for detection. Fractions containing the same product were combined, concentrated by evaporation to remove solvents and the aqueous residues were lyophilized. Fractions 25–27 were combined and yielded 23 mg. of the tetrahydro factor B. Fractions 62–72 were combined and yielded 33 mg. of tetrahydrodeoxy factor B (isomer 1). Fractions 78–83 were combined to yield 4.6 mg. of tetrahydrodeoxy factor B (isomer 2). Fractions 97–107 were combined to yield 7.5 mg. of the tetrahydrodeoxy factor B (isomer 3).

Tetrahydro Factor B (formula 1e)
FD/MS: (M+H)+ = 286.
$^1$H NMR (270 MHz, D$_2$O): δ(ppm) 1.58–1.92 (7H, overlapped), 2.08 (2H, m), 2.29 (1H, m), 2.49 (3H, t), 3.68 (1H, m), 4.07 (1H, dd), 4.19 (1H, m).

Tetrahydrodeoxy Factor B (formula 1d) isomer 1
FD/MS: (M+H)+ = 270.
$^1$H NMR (270 MHz, D$_2$O): δ(ppm) 1.48–2.17 (12H, overlapped), 2.48 (3H, m), 3.55 (1H, m), 4.15 (1H, t).

Tetrahydrodeoxy Factor B, isomer 2
FD/MS: (M+H)+ = 270.
$^1$H NMR (270 MHz, D$_2$O): δ(ppm) 1.4 (2H, m), 1.5–2.1 (9H, overlapped), 2.25 (1H, m), 2.44 (3H, m), 3.56 (1H, m), 5.10 (1H, s).

Tetrahydrodeoxy Factor B, isomer 3
FD/MS: (M+H)+ = 270.
$^1$H NMR (270 MHz, D$_2$O): δ(ppm) 1.33 (2H, m), 1.5–1.7 (5H, overlapped), 1.80 (2H, m), 1.92 (1H, m), 2.09 (2H, m), 2.25 (1H, d), 2.43 (2H, t), 3.54 (1H, m), 5.08 (1H, s).

EXAMPLE 3

Deoxy Factor A and Tetrahydrodeoxy Factor A via Hydrogenation of Factor A in HCl A solution of 5 mg. of factor A in 5 ml. of 1N hydrochloric acid was hydrogenated in the presence of Pt catalyst (10 mg. of PtO$_2$ prereduced) under one atmosphere of hydrogen pressure. The hydrogenation was discontinued when about one mole of hydrogen per mole of factor A was absorbed (ca. 2 hours). The reaction mixture was filtered to remove the catalyst and the filtrate analyzed by HPLC. The reduction product mixture contained unreduced factor A, deoxy factor A, and tetrahydrodeoxy factor A.

EXAMPLE 4

3-Carboxyoctahydro-5-oxo-8-hydroxy-6-indolizinepropanoic acid dimethyl ester

To a solution of 500 mg. of A-58365 factor A dimethyl ester in 100 ml. of methyl alcohol was added 0.5 g. of 5% rhodium on alumina and the suspension was placed in a Parr high pressure stainless steel autoclave and hydrogenated at 110° C. for 12 hr. under 500 psi. of hydrogen. After reduction was completed the catalyst was filtered and the filtrate concentrated by evaporation. The concentrate was chromatographed over a 1"OD×12" reverse phase HPLC column (ZORBAX ODS, E. I. Dupont) eluted with 10% acetonitrile-water at a rate of 10 ml./min. The chromatography was monitored via UV using absorption of 210 and 254 nm. Fractions were pooled on the basis of analytical HPLC (4.6 mm ID×25 cm. column of C$_{18}$ reverse phase, ZORBAX ODS eluted with 12% aq. acetonitrile at 2 ml./min., and using UV absorption at 210 nm.). The pooled fractions were concentrated by evaporation to an aqueous concentrate of 50 ml. volume. The concentrate was extracted twice with 100 ml. portions of butyl acetate and once with 50 ml. of butyl acetate. The extracts were combined and evaporated to dryness to yield 102.8 mg. of the dimethyl ester of 3-carboxyoctahydro-5-oxo-8-hydroxy-6-indolizinepropanoic acid. The product was obtained crystalline from methylene chloride-diethyl ether.

FD/MS: (M+) 299.
$[α]_{589}^{25°}$ −18.0° (5 mg./ml. CH$_3$OH).
$[α]_{365}^{25°}$ −49.6° (5 mg./ml. CH$_3$OH).
IR(KBr): 3362–3365, 3,000, 2943, 2925, 2881, 1751, 1733, 1692, 1629, 1594, 1462, 1449, 1441, 1429, 1383, 1357, 1342, 1306, 1286, 1256, 1226, 1202, 1173, 1123, 1106, 1093, 1077, 1063, 1043, 1028, 1006, 994, 962, 938, 897, 867, 857, 796, 759, 712, and 673 cm$^{-1}$.
$^1$H NMR (360 MHz, D$_2$O): δ(ppm) 1.74 (1H, m), 1.83 (1H, sextet), 2.05 (2H, m), 2.11 (1H, m), 2.16 (1H, m), 2.26 (1H, m), 2.40 (1H, m), 2.45 (1H, m), 2.54 (2H, t), 3.71 (3H, s), 3.77 (3H, s), 3.84 (1H, td), 4.27 (1H, m), 4.48 (1H, d).

X-Ray crystallography of crystalline product indicated the product has the following relative configuration.

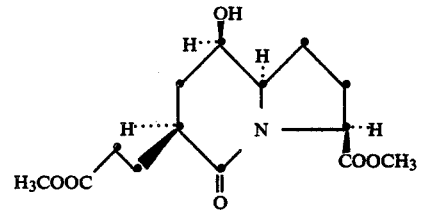

EXAMPLE 5

Hydrogenation of Factor A over Rhodium

To a solution of 51.7 mg. of factor A in 100 ml. of methyl alcohol were added 50 mg. of 5% Rh on alumina and the mixture was hydrogenated for 12 hours at a temperature of about 160° C. under a hydrogen pressure of 500 psi. The reduction mixture was filtered, dried, evaporated and chromatographed by reverse phase HPLC using a Dupont Zorbax ODS column (9.4 mm ID×25 cm.). The flow rate was 4 ml./min. and monitoring was done in the UV at 210 nm. and 325 nm. The mobile phase was A: 50% acetonitrile with 0.2% formic acid and C: 0.2% formic acid. The solvent program was 20 min. with C, 20 min. with 0–10% A, and 15 min. with 10–25% A. The flow rate was 1.5 min./fraction.

Fractions 35 and 36 were combined, concentrated and lyophilized to yield 3.7 mg. of a mixture of two isomeric forms of tetrahydro factor A in a ratio of 1.6:1. Other reduction products observed in the reduction were the monomethyl esters of an isomeric mixture of tetrahydro factor A, a mixture of two isomeric forms of tetrahydrodeoxy factor A, and a mono methyl ester of tetrahydrodeoxy factor A. The dimethyl ester of unreduced factor A was also present.

EXAMPLE 6

Production and Isolation of A58365 Factors

A lyophilized pellet of *S. chromofuscus* NRRL 15098 was used to inoculate 50 ml. of a sterilized vegetative medium of three percent trypticase soy broth containing one percent glucose. The inoculated medium was incubated at 30° C. for 48 hours with shaking. This vegetative medium was used to inoculate bump media as follows. Two, 2,000 ml. flasks each containing 400 ml. of three percent trypticase soy broth with one percent glucose added were each inoculated with 10 ml. of the vegetative medium. The bump cultures were then incubated for 24 hours at a temperature of 30° C.

Both of the bump cultures were used to inoculate 100 liters of production medium. The production medium had the following composition.

| Ingredient | Concentration (g./l.) |
|---|---|
| Dow-Corning antifoam A | 0.2 |
| Potato Dextrin | 35 |
| Yeast | 0.25 |
| OM Peptone[1] | 20 |
| $CoCl_2.6H_2O$ | 0.01 |
| L-Proline | 4 |
| N-Z Amine A[2] | 4 |
| Deionized water | qs. to 100 l. |

[1] OM Peptone is a soluble meat peptone, Amber Laboratories, Juneau, WI.
[2] N-Z Amine A is an enzymatic hydrolysate of casein, Humko Sheffield Chemical, Lyndhurst, NJ.

The pH of the medium was adjusted to 7.0 with 5N sodium hydroxide before sterilization. After sterilization the medium was inoculated with the bump media described above and the production fermentation was allowed to proceed at a temperature of 25° C. for 90 hours. During the fermentation sterile air was passed through the medium, with stirring, at a rate sufficient to maintain the dissolved oxygen content of the medium at about 30% to about 40% of air saturation.

The pH of the medium increased during the fermentation to a terminal pH of 8.3.

During the fermentation the medium was assayed for A58365 factor content by employing the HPLC system described hereinabove. The factors were detected by fluorescence using a Schoeffel Model FS970 spectrophotofluorometer at the wave length $\lambda exc.=327$ nm. with a 370 nm. cutoff filter. The production medium assayed for about 11.5 mcg./ml. after the 90 hour fermentation period.

Three, 100-liter fermentations carried out as described above were separately acidified in the fermentors to pH 2.0 with concentrated hydrochloric acid. The acidified whole broths were combined and filtered with the aid of 2% Hyflo filter aid. The pH of the filtered broth was adjusted to 7.0 with 5N sodium hydroxide. The nonfunctional resin Diaion HP-20 was added to the neutral broth in an amount corresponding to one-tenth the volume of the filtered broth and the resin-broth mixture was stirred for two hours. The broth was separated from the resin and acidified to pH 2.0 with 5N hydrochloric acid. The acidified broth was chilled and filtered to remove inactive precipitates. The acidified broth was applied to a 20'×4" i.d. column containing 20 l. of Diaion HP20 and the effluent discarded. The column was next washed with 60 l. of 0.3% aqueous formic acid and the effluent discarded. The A58365 factors were then eluted with a 100 l. gradient from water-formic acid (99.7:0.3; v:v:v:) to acetonitrile-water-formic acid (20:79.7:0.3; v:v:v.) and 2 l. fractions were collected. Fractions 27 to 48 containing factor A were pooled and concentrated in vacuo to a volume of 750 ml. Elution was continued with 20 liters of acetonitrile-water-formic acid (20:79.7:0.3). Fractions 56 to 63 containing factor B were pooled and concentrated to a volume of 350 ml.

The factor A containing concentrate was applied to a 9.3 cm.×80 cm. (5 l.) column of Dowex 50W×2 ($H^{30}$) and the column was eluted with about 17 l. of deionized water. One-liter fractions from 9 to 15 liters of eluted volume containing factor A were collected, pooled and concentrated to about 200 ml.

The factor A concentrate (pH 2-3) was filtered and chromatographed on reverse phase HPLC on a 8 cm.×1 m. column (Jobin Yvon Chromatospac Prep instrument) containing approximately 2.5 kg. (4-4.5 l.) of octadecylsilanized Whatman LP-1 silica gel. The column was developed first with two liters of formic acid-water (0.3:99.7, v:v), then with 5 liters of acetonitrile-formic acid-water (1.0:0.3:98.7, v:v:v), and, finally with 20 l. of acetonitrile-formic acid-water (2.5:0.3:97.2, v:v:v). Fractions of 500 ml. volume were collected. Fractions 32-44 containing factor A were pooled and concentrated by evaporation to a volume of 200 ml.

The factor A concentrate from HPLC was applied to 2.5 cm.×30 cm. (180 ml.) column of 100-200 mesh BioRex 5 ($Cl^-$) resin (BioRad Laboratories, Richmond, CA). The resin was washed with deionized water and both the wash and effluent were discarded. The column was developed with 400 ml. of 0.20M sodium chloride and then with 2200 ml. of 0.35M sodium chloride. Fractions of 20 ml. in volume were collected and fractions 106-140 containing pure factor A were pooled. The pH of the pooled fractions was adjusted to 2.3 with 1N hydrochloric acid and the acidified pool was applied to a 2.8 cm.×19 cm. (120 ml.) column of Diaion HP20 set in 0.01N hydrochloric acid. The column was washed first with 100 ml. of deionized water acidified to pH 2.3 with dilute hydrochloric acid, then with 220 ml. of deionized water (pH 5.9), and was then eluted with 340 ml. of acetonitrile-water (15:85, v:v). After multiple fractions totaling about 180 ml. in volume had been collected, the fractions from 0-180 ml. of effluate were collected, combined, concentrated by evaporation and lyophilized to give 1.31 g. of pure factor A.

The concentrate of pooled factor B containing fractions, eluted from the Diaion HP-20 column as described above, was applied to a 9.3 cm.×80 cm. (5 l.) column of Dowex 50W×2 ($H^+$ cycle) resin. The column was eluted with 32 l. of deionized water and factor B was collected in one liter fractions from 10 to 14 liters of eluate. The active fractions were combined and concentrated to a volume of about 250 ml.

The A58365 factor B containing concentrate was then subjected to the same reverse phase HPLC as described above for the purification of factor A. The column was developed first with two liters of formic acid-water (0.3:99.7% by vol.), next with acetonitrile-formic acid-water (6.0:0.3:93.7%) by vol.) and then with acetonitrile-formic acid-water (15.0:0.3:84.7, % by vol.). Multiple fractions of about 500 ml. were collected. Fraction 24 containing factor B was concentrated by evaporation to a volume of 100 ml.

The concentrate of factor B was further purified on an anion exchange resin as follows. A 2.0 cm. i.d.×25 cm. column packed with BioRex 5 (Cl⁻) anion exchange resin was charged with the concentrate and the column was eluted first with 200 ml. of 0.2M sodium chloride followed by elution with 1600 ml. of 0.35M sodium chloride. Multiple fractions of 10 ml. volume were collected and fractions 193–210 were pooled. The pH of the pooled fractions was adjusted to pH 2.3 with 1N hydrochloric acid and the acidified pool was applied to an 8 mm. i.d.×20 cm. (10 ml.) Diaion HP-20 column set in 0.01N hydrochloric acid. The column was washed first with 300 ml. of deionized water (adjusted to pH 2.3) then with 14 ml. of deionized water (pH 5.9). The effluent and wash were discarded and factor B was eluted with 44 ml. of acetonitrile-water, (15:85% by vol.). Multiple fractions of 2 ml. volume were collected. Fractions 8 to 11 were pooled and concentrated to a volume of 1 ml. The concentrate was lyophilized to give 2.9 mg. of pure factor B.

EXAMPLE 7

O-Acetyl Factor A

Factor A (100 mg.) was mixed at room temperature with 12.5 ml. of pyridine and 12.5 ml. of acetic anhydride to form the O-acetyl derivative, 3-carboxy-8-acetoxytetrahydroindolizine-6-propanoic acid. The product was purified via reverse phase HPLC using a 1″OD×12″ stainless steel Zorbax ODS column (12μ particle size). Solvent A, 0.2% formic acid: water; Solvent B, 0.2% formic acid: 8% acetonitrile: water Multiple fractions of 20 ml. volume were collected (2 min/fraction) and the separation was monitored at 310 nm and 254 nm. Fractions 1–35 were collected with Solvent A and fractions 36–92 with Solvent B. The O-acetyl factor A was collected in fractions 56–83.

FD/MS (M+H)⁺ = 310.

¹H NMR (270 MHz, D₂O): δ(ppm) 2.35 (3H, s), ca. 2.40 (1H, m), 2.62 (1H, m), 2.69 (2H, t), 2.80 (2H, m), 3.11 (2H, t), 5.15 (1H, dd, J=10.3 Hz), 7.44 (1H, s).

EXAMPLE 8

Preparation of Deoxy factor A and Tetrahydrodeoxy factor A via O-acetyl factor A To a solution of 4.7 mg. of O-acetyl factor A in 4.5 ml. of 1N hydrochloric acid were added 10 mg. of platinum oxide catalyst (prereduced). The mixture was hydrogenated for about 20 minutes in an atmosphere of hydrogen. The catalyst was filtered and the reduction product mixture was found to contain 68% deoxy factor A, 29% tetrahydrodeoxy factor A, and 3% factor A via analytical reverse phase HPLC.

EXAMPLE 9

Deoxy factor B via O-Acetyl factor B

By following the conditions described above in Examples 7 and 8, factor B is acetylated to the O-acetyl factor B and the latter is hydrogenated over PtO₂ (prereduced) in 1N HCl to provide deoxy factor B.

We claim:

1. The compound of the formula

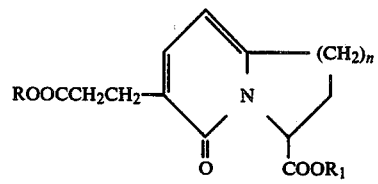

wherein n is 1 or 2; R and R₁ independently are hydrogen, $C_1$-$C_6$ alkyl, indanyl, phthalidyl, or an acyloxymethyl group of the formula

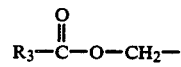

wherein $R_3$ is $C_1$-$C_4$ alkyl, phenyl, halophenyl, $C_1$-$C_4$ alkylphenyl, $C_1$-$C_4$ alkoxyphenyl, or 3,4-methylenedioxyphenyl; and when either or both of R and R₁ is or are hydrogen, and the pharmaceutically acceptable non-toxic salts thereof.

2. The compound of claim 1 wherein R and R₁ are both hydrogen, and the pharmaceutically acceptable non-toxic salts thereof.

3. The compound of claim 2 wherein n is 1 and the pharmaceutically acceptable non-toxic salts thereof.

4. The compound of claim 2 wherein n is 2 and the pharmaceutically acceptable non-toxic salts thereof.

* * * * *